United States Patent [19]
Miller et al.

[11] Patent Number: 5,087,264
[45] Date of Patent: Feb. 11, 1992

[54] VENOUS VALVE-INCISING DEVICE

[75] Inventors: Arnold Miller, Boston, Mass.; David E. Barlow, Hicksville, N.Y.; Tatsuya Saitoh, Funabashi, Japan

[73] Assignee: Olympus Optical Co., Ltd., Tokyo, Japan

[21] Appl. No.: 543,229

[22] Filed: Jun. 25, 1990

[30] Foreign Application Priority Data

Nov. 28, 1989 [JP] Japan .................. 1-308475

[51] Int. Cl.⁵ ........................................ A61B 17/32
[52] U.S. Cl. ........................................ 606/159; 604/22
[58] Field of Search ............... 606/159, 170, 167; 604/22; 128/24 A; 30/296.1

[56] References Cited

U.S. PATENT DOCUMENTS

| | | | |
|---|---|---|---|
| 4,493,321 | 1/1985 | Leather | 606/159 |
| 4,497,320 | 2/1985 | Nicholson et al. | |
| 4,768,508 | 9/1988 | Chin et al. | 604/22 |
| 4,952,215 | 8/1990 | Ouriel et al. | 606/170 |

FOREIGN PATENT DOCUMENTS 0048812 12/1988 Fed. Rep. of Germany ...... 606/159
63-38505 3/1988 Japan.

OTHER PUBLICATIONS

LeMaibre, *In Situ Bypass Grafting*, Vascutech, Inc., Andover, Mass., 1987, extracts including pp. 53, 54.

*Primary Examiner*—C. Fred Rosenbaum
*Assistant Examiner*—William W. Lewis
*Attorney, Agent, or Firm*—Frishauf, Holtz, Goodman & Woodward

[57] ABSTRACT

A venous valve-incising device is made up of a flexible insertion member having a distal end, a hard tip attached to the distal end of the insertion member, and a coupling member for detachably coupling the hard tip and the distal end of the insertion member together. The hard tip includes a rod portion, and a curved portion curved at a predetermined angle with respect to the axis of the road portion and having a rear edge on which a cutting edge is formed.

22 Claims, 3 Drawing Sheets

VENOUS VALVE-INCISING DEVICE

BACKGROUND OF THE INVENTION

1. Field of the Invention

The present invention relates to an incising device for incising or cutting out the valves of a vein.

2. Description of the Related Art

If an artery is clogged due to atheroma formed at a branch blood vessel, the surgical operation is carried out to provide a bypass for the closed portion of the artery by utilizing a saphenous vein. Since a vein has valves for causing the blood to flow in one direction only, the valves have to be cut out before using the vein as a bypass.

The surgical operation for cutting out the venous valves is carried out as follows. First two openings are formed at positions which are upstream and downstream of that portion of the vein from which the valves are to be cut out. At this time, the vein is clamped in the neighborhood of the two openings, so as to stop the blood flow. The incising device is inserted from the upstream opening, and is then pulled back for the incision of the valves after it is introduced up to a predetermined point. Since the incising device has a cutting edge directed backward, the valves are incised or cut out when the incising device is pulled back.

A typical example of a conventional venous valve-incising device of this type is disclosed in Published Unexamined Japanese Utility Model Application No. 63-38505. In the device disclosed in this reference, a guide tube and cutting blades are coupled to the tip end of a flexible sheath. The device permits the number of cutting blades to be changed in accordance with the incision area, but does not allow the use of suitable cutting blades in accordance with the size of the vein or the state of the venous valves.

In the surgical operation for cutting out the venous valves, the operator can visually confirm the shape and other features of the venous valves by inserting a fiber scope into the vein beforehand. Therefore, the operator can select a cutting edge having the most suitable shape for the treatment, before he or she actually inserts the incising device into the vein. However, once the incising device is inserted in the vein, the operator is not allowed to replace the cutting edge with another. Therefore, if the replacement of the cutting edge is absolutely necessary, the operator has to pull the incising device out of the vein through the upstream opening, replace the cutting edge with another, and insert the incising device again into the vein. When the incising device is pulled, the cutting edge may incise the valves in an undesirable manner. In some cases, the cutting edge may catch on a side branch and tear it.

SUMMARY OF THE INVENTION

Accordingly, an object of the present invention is to provide a venous valve-incising device which permits selection and easy replacement of a cutting edge having a suitable shape and size for a vein under treatment, even after the incising device is actually inserted into the vein.

This object is achieved by a venous valve-incising device which comprises: a flexible insertion member having a distal end; a hard tip attached to the distal end of the insertion member and coupling means for detachably coupling the hard tip and the distal end together, the hard tip including a rod portion, and a curved portion curved at a predetermined angle with respect to the axis of the rod portion and having a rear edge on which a cutting edge is formed.

The venous valve-incising device is used as follows. The distal end of the insertion member (e.g., a thin wire rope) is first inserted into a vein from an upstream opening and is guided out of the vein from a downstream opening. Then, a hard tip having a cutting edge is coupled to the distal end of the insertion member, in accordance with the size and shape of the venous valves. Thereafter, the insertion member is pulled back into the vein and moved toward the upstream opening, i.e., closer to the operator, to thereby incise the venous valves. If the operator wants to replace the cutting edge with another, the insertion member is pushed, so as to cause the hard tip at the distal end of the insertion member to come out of the vein, and the hard tip is replaced with another.

When the insertion member is initially inserted in the vein, a bullet-shaped guide tip having no cutting edge is coupled to the distal end of the insertion member. Due to the use of such a guide tip, the flexible insertion member can be inserted in the vein, with no danger of damaging the inner wall of the vein.

Additional objects an advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Figure 1:
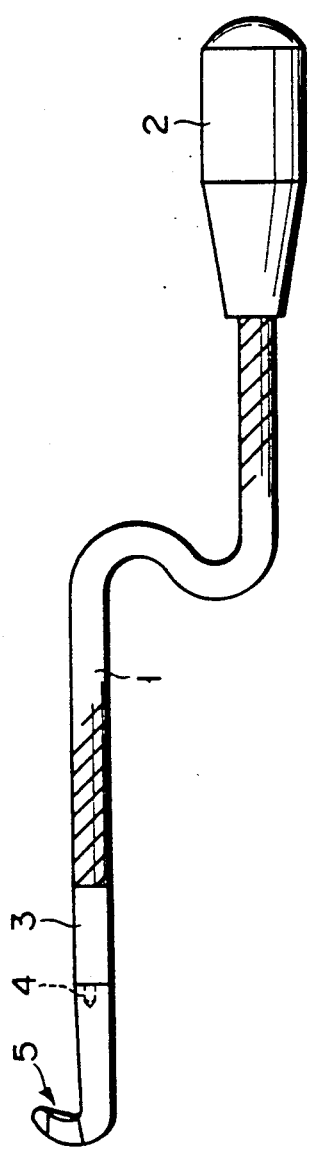
FIG. 1 is a side view showing the entire construction of a venous valve-incising device according to the first embodiment of the present invention.

FIGS. 1 through 5 illustrate a venous valve-incising device according to the first embodiment of the present invention. The venous valve-incising device comprises a flexible insertion member 1 having a predetermined length and formed of e.g. a thin wire rope. A handle 2 is fixed to the proximal end of the flexible insertion member 1, while a hard section 3 is formed at the distal end thereof. A male screw 4 (i.e., part of coupling means) is projected from the distal end of the hard section 3, and a hard tip 5 is detachably coupled to the male screw 4.

The hard tip 5 has a curved portion 6 at the tip end thereof, and a cutting edge 7 is formed on the rear edge of the curved portion 6. The curved portion 6 is located at the tip end of the rod portion 8 of the hard tip 5. The curved portion 6 is curved with respect to the rod portion 8 at an angle $\theta$ which is less than 90°. In other words, the curved portion 6 is slanted with reference to the straight portion 8 such that it is directed toward the proximal end of the flexible insertion member 1. The tip end of the curved portion 6 is a semi-spherical portion having a smooth surface, and the cutting edge 7 mentioned above is formed on the inner side of the curved portion 6, i.e., on that side of the curved portion 6 which is directed toward the proximal end of the flexible insertion member 1.

A female screw 9 is formed at the bottom end of the rod portion 8 of the hard tip 5. The hard tip 5 is detachably coupled to the flexible insertion member 1, with the female screw 9 engaged with the male screw 4 projected from the distal end of the flexible insertion member 1.

Figure 3:
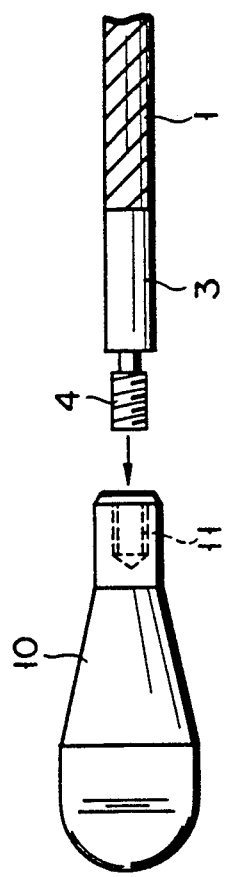
FIG. 3 is an exploded side view of the coupling construction between a guide tip and the insertion member.

FIG. 3 shows a guide tip 10 which can be attached to the hard section 3 of the flexible insertion member 1 in place of the hard tip 5 mentioned above. The guide tip 10 is shaped like a bullet and has no cutting edge. A female screw 11 adapted for engagement with the male screw 4 at the distal end of the hard section 3 is formed at the bottom end of the bullet-shaped guide tip 10.

Figure 4:
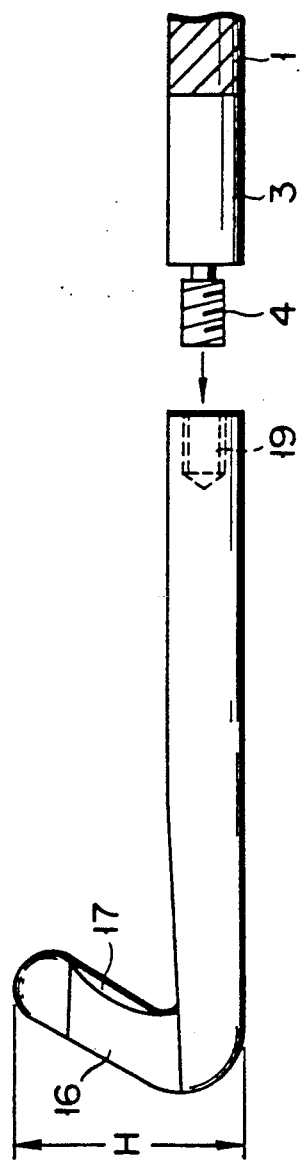
FIG. 4 is an exploded side view of the coupling construction between another type of hard tip and the insertion member.

FIG. 4 shows a hard tip 15 which is different in size from the hard tip 5 mentioned above. The hard tip 15 also has a curved portion 16 located at the distal end thereof. The tip end of the curved portion 16 is slanted toward the bottom end of the hard tip 5, and a cutting edge 17 is formed on the inner side of the curved portion 16. A female screw 19 adapted for engagement with the male screw 4 projected from the distal end of the hard section 3 is formed at the bottom end of the hard tip 15. It should be noted that the hard tip 15 differs from the hard tip 5 shown in FIG. 2, in both height H of the curved portion 16 and the length of the cutting edge 17.

A description will now be given of the manner in which the venous valve-incising device of the first embodiment is used and also of the operation of the device.

Figure 5:
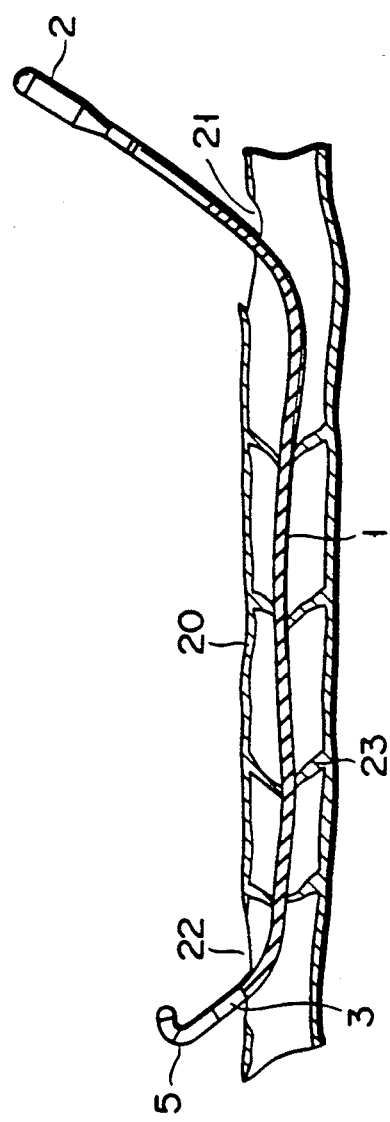
FIG. 5 is a side view showing the state where the venous valve-incising device inserted in a vein.

Referring to FIG. 5, a vein 20 to be treated is clamped at upstream and downstream points (the clamped points being not shown), so as to stop the blood flow. Then, openings 21 and 22 are formed at locations close to the clamped upstream and downstream points, respectively.

Next, the bullet-shaped guide tip 10 shown in FIG. 3 is coupled to the distal end of the flexible insertion member 1 by threadably engaging its female screw 11 with the male screw 4 projected from the distal end of the flexible insertion member 1. Thereafter, the flexible insertion member 1 is inserted into the vein 20 from the upstream opening 21, with the guide tip 10 leading forward, until the distal end of the flexible insertion member comes out of the vein 20 from the downstream opening 22, when the bullet-shaped guide tip 10, followed by the insertion member 1, is pushed into the vein 20 from the upstream opening 21, it advances while simultaneously opening the venous valves 23, and is pushed out of the vein 20 from the downstream opening 22.

Figure 2:
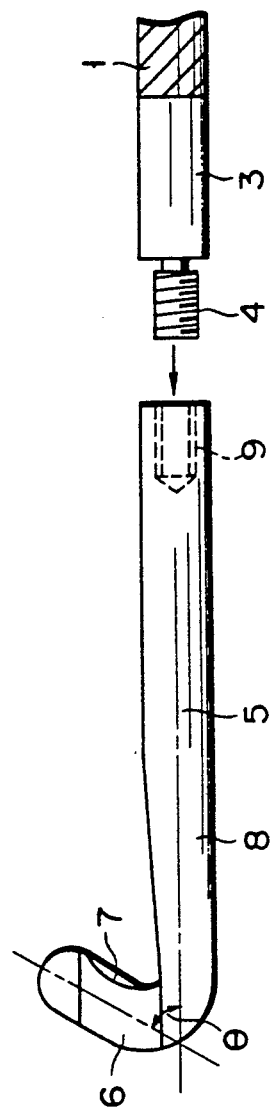
FIG. 2 is an exploded side view of the coupling construction between one type of hard tip and a flexible insertion member.

After the bullet-shaped guide tip 10 comes out of the downstream opening 22, it is removed from the distal end of the flexible insertion member 1. Instead, the hard tip 5, such as that shown in FIG. 2, is coupled. That is, the female screw 9 formed at the bottom end of the hard tip 5 is threadably engaged with the male screw 4 projected from the distal end of the flexible insertion member 1.

After coupling the hard tip 5 in this fashion, the handle 2 is pulled backward, to thereby pull back the flexible insertion member 1 toward the upstream location of the vein 20. As a result, the hard tip 5 enters the interior of the vein 2 from the downstream opening 22 and moves through the vein 20 toward the upstream location. At this time, the cutting edge 7 formed at the curved portion 6 and directed toward the proximal end of the insertion member 1 cuts out the valves 23 in the vein 20.

The manner in which the cutting edge 7 of the curved portion 6 cuts out the venous valves 23 is monitored by use of a blood vessel fiber scope (not shown) which is inserted into the vein 20 from the downstream opening 22 beforehand. Thus, the operator can carry out the incising operation while visually confirming the state in which the venous valves 23 are being cut out.

Before the venous valve-incising device is inserted into the vein 20, the blood vessel fiber scope is inserted into the vein 20 from the downstream opening 22. Since, therefore, the operator can examine the condition of the venous valves 23 before the insertion of the venous valve-incising device, he or she can select a hard tip having the most suitable size for the treatment of the vein 23. More specifically, after the bullet-shaped guide tip 10 is made to come out of the downstream opening 22, the operator can select the most suitable hard tip from among various types of hard tips of different sizes and shapes, and couple the selected hard tip to the flexible insertion member 1.

If it is found out during the incising operation that the tip selected and coupled is not suitable, then the operator pushes the flexible insertion member 1 while holding the handle until the hard tip comes out of the downstream opening 22, and replaces the hard tip with another which the operator thinks more suitable. It should be noted that this replacement operation does not undesirably damage the inner wall of the vein since the hard tip is returned to the downstream location through the already-incised venous valves 23.

As mentioned above, the venous valve-incising device of the first embodiment of the present invention permits the operator to select and use a hard tip whose cutting edge is suitable for the size and shape of the venous valves. Therefore, the operation can be carried out in the most desirable state. Even if it is found out during the valve-incising operation that the hard tip which the operator uses is not suitable, such a hard tip can be easily replaced with another. It should be noted that only the hard tip at the distal end of the insertion member 1 is replaced with another, so that it is not necessary to prepare a number of special members or parts for that replacement.

Figure 6:
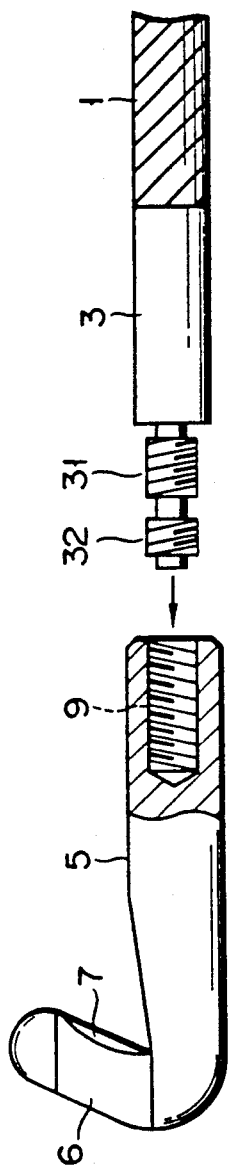
FIG. 6 is a exploded side view of the coupling construction between the hard tip used in the second embodiment and the insertion member.

FIG. 6 shows the second embodiment of the present invention.

In the second embodiment, the screw portion (i.e., part of coupling means) formed at the distal end of the hard section 3 of the flexible insertion member 1 is made up of a first screw 31, and a second screw 32 spaced from the first screw 31 but having threads formed in the same direction as the first screw 31. The first and second screws 31 and 32 can be threadably engaged with the female screw 9 formed at the bottom end of the hard tip 5.

According to the second embodiment, the hard tip 5 hardly disengages from the flexible insertion member 1 since the first and second male screws 31 and 32 firmly engage with the female screw 9.

Figure 7:
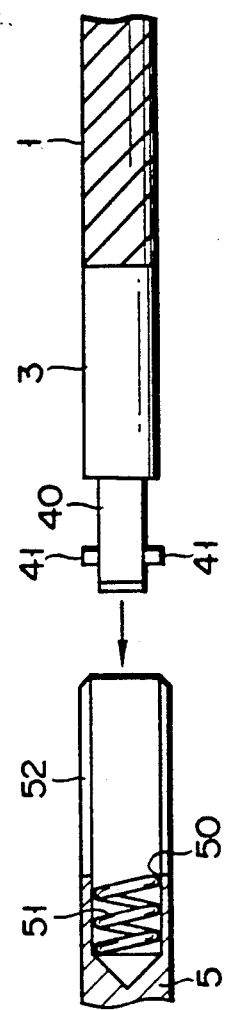
FIGS. 7 and 8 are an exploded sectional view and a side view, respectively, both illustrating the coupling construction between a hard tip used in the third embodiment and the insertion member.
Figure 8:
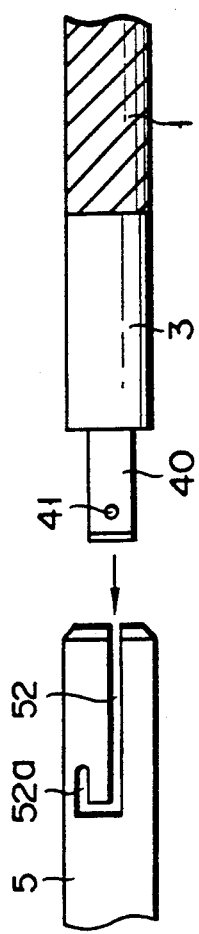

The third embodiment of the present invention will now be described, with reference to FIGS. 7 and 8.

In a venous valve-incising device of the third embodiment, an insertion rod 40 is projected from the distal end of the hard section 3 of the flexible insertion member 1. The insertion rod 40 has a pair of engagement pins 41 projected perpendicular to the axial direction of the insertion rod 40. An insertion hole 50 adapted to receive the insertion rod 40 is formed in the bottom end portion of the hard tip 5. A spring 51 is located in the bottom of the insertion hole 50, and a pair of substantially "J"-shaped slits 52 are formed in the wall defining the insertion hole 50, so as to guide and stop the engagement pins 41. The rear end of each slit 52 is open in the end face of tip 5, while the front end of each slit 52 is bent to form a hook portion 52a.

To couple the tip 5 to the hard section 3, the insertion rod 40 at the distal end of the hard section 3 of the flexible insertion member 1 is fitted in the insertion hole 50 of the hard tip 5. Then, the engagement pins 41 of the insertion rod 40 are inserted into the respective "J"-shaped slits 52 of the tip 5. In this state, the insertion rod 40 is pushed into the insertion hole 50 of the hard tip 5 until the engagement pins 41 abut the bottom faces of the J-shaped slits 52. When the insertion rod 40 is being pushed in, its tip end advances while compressing the spring 51. When the engagement pins 41 have abutted the bottom faces of the J-shaped slits 52, the hard tip 5 and the flexible insertion member 1 are rotated relative to each other, so as to cause the engagement pins 41 to advance into the hook portions 52a of the J-shaped slits 52. Since, in this state, the distal end of the flexible insertion member 1 is pressed by the spring 51, the engagement pins 41 are prevented from coming out of the hook portions 52a of the slits 52. Thus, the hard tip 5 can be reliably coupled to the distal end of the flexible insertion member 1.

According to the third embodiment, the engagement or disengagement of the hard tip 5 with reference to the flexible insertion member is very easy, in comparison with the case where a screw type coupling structure is employed.

Needless to say, the present invention is not limited to the embodiments mentioned above. It may be embodied or modified in various manners without departing from the spirit and scope of the invention, as will be obvious to those skilled in the art.

What is claimed is:

1. A venous valve-incising device for incising venous valves from a vein, comprising:
   a flexible insertion member having a distal end;
   a plurality of hard tips, each tip being attachable to the distal end of the insertion member, each of said hard tips including:
   a rod portion having an axis; and
   a curved end portion which is curved at a predetermined angle with respect to said axis of said rod portion, said curved end portion having a front portion and a rear edge portion and a cutting blade formed on said rear edge portion;
   said cutting blades of each of said hard tips having a size and shape, at least one of said size and shape of each cutting blade being different from that of another cutting blade; and
   coupling means for detachably coupling the rod portion of a selected one of said plurality of said hard tips to the distal end of said insertion member, said selected one of said hard tips being chosen based on the size of the vein and the shape of the venous valve which is to be incised.

2. A venous valve-incising device according to claim 1, wherein each of said cutting blades has a different length.

3. A venous valve-incising device according to claim 1, wherein said curved portion of said selected hard tip is curved backward in such a manner as to form an acute angle with reference to the axis of said rod portion.

4. A venous valve-incising device according to claim 1, wherein the distal end of said insertion member is formed of a hard material.

5. A venous valve-incising device according to claim 4, wherein aid coupling means includes a male screw portion formed on the hard distal end of the insertion member, and a female screw portion formed on the rod portion of said hard tip.

6. A venous valve-incising device according to claim 5, wherein said male screw portion includes two screw parts.

7. A venous valve-incising device according to claim 4, wherein said coupling means comprises:
   an insertion hole and slits formed in one of the distal end of the insertion member and the rod portion of each of said plurality of hard tips; and
   an insertion rod and engagement pins formed in the other of said hard distal end of said insertion member, and the rod portion of each of said plurality of hard tips, said insertion rod being insertable into the insertion hole, and said engagement pins fitting into respective slits upon insertion of said insertion rod into said insertion hole.

8. A venous vale-incising device according to claim 7, further comprising urging means, positioned in said insertion hole, for retaining said insertion rod in said insertion hole.

9. A venous valve-incising device according to claim 8, wherein said urging means is compressible; and wherein each of said slits is substantially J-shaped, each slit comprising a vertical portion having first and second end portions and a hooked portion formed at said first end portion of said vertical portion, said second end portion being open, whereby said engagement pins engage with and are held at the hook portions of the slits after the insertion rid is pushed into the insertion hole while compressing the urging means.

10. A venous valve-incising device according to claim 7, wherein said insertion hole and slits are formed in the rod portion of each of said plurality of hard tips.

11. A venous valve-incising device for exercising venous valve from a vein, comprising:
   a flexible insertion member having a distal end, said distal end being formed of a hard material;

a hard tip attachable to the distal end of said insertion member, said hard tip including:
  a rod portion having an axis; and
  a curved portion which is curved at a predetermined angle with respect to said axis of the rod portion, said curved end portion having a front portion and a rear edge portion, and a cutting blade formed on said rear edge portion; and
coupling means for detachably coupling the rod portion of the hard tip to the distal end of said insertion member, said coupling means including a male screw portion formed on the hard distal end of the insertion member, and a female screw portion formed on the rod portion of said hard tip, said male screw portion including two screw parts.

12. A venous valve-incising device according to claim 11, wherein the curved portion of said selected hard tip is curved backward in such a manner as to form an acute angle with reference to the axis of said rod portion.

13. A venous valve-incising device for exercising venous valve from a vein, comprising:
a flexible insertion member having a distal end, said distal end being formed of a hard material;
a hard tip attachable to the distal end of said insertion member, said hard tip including:
  a rod portion having an axis; and
  a curved portion which is curved at a predetermined angle with respect to said axis of the rod portion, said curved end portion having a front portion and a rear edge portion, and a cutting blade formed on said rear edge portion; and
coupling means for detachably coupling the rod portion of the hard tip to the distal end of said insertion member, said coupling means including:
  an insertion hole and slits formed in one of the distal end of the insertion member and the rod portion of said hard tip;
  an insertion rod and engagement pins formed on the other of said hard distal end of the insertion member and the rod portion of said hard tip; and
  said insertion rod being insertable into the insertion hole and said engagement pins fitting into respective slits upon insertion of said insertion rod into said insertion hole.

14. A venous valve-incising device according to claim 13, further comprising urging means, positioned in said insertion hole, for retaining said insertion rid in said insertion hole.

15. A venous valve-incising device according to claim 14, wherein:
said urging means is compressible; and
each of said slits is substantially J-shaped, each slit comprising a vertical portion having first and second end portions and a hooked portion formed at said first end portion of said vertical portion, said second end portion being open, whereby said engagement pins engage with and are held at the hook portions of the slits after the insertion rod is pushed into the insertion hole while compressing the urging means.

16. A venous valve-incising device according to claim 13, wherein said insertion hole and slits are formed in the rod portion of said hard tip.

17. A venous valve-incising device for incising a valve in a vein, said valve being positioned between a pair of incisions made in said vein which are respectively upstream and downstream of said valve, in the direction of blood flow through said vein, the venous valve-incising device comprising:
a flexible insertion member having a distal end, said distal end being formed of a hard material;
a plurality of hard tips, each being attachable to said distal end of said insertion member, each of said hard tips including:
  a rod portion having an axis;
  a curved end portion which is curved at a predetermined angle with respect to said axis of said rod portion, said curved end portion having a front portion and a rear edge portion and a cutting blade formed on said rear edge portion;
said cutting blades of each of said hard tips having a size and shape, at least one of said size and shape of each cutting blade being different from that of another cutting blade; and
coupling means for detachably coupling the rod portion of a selected one of said plurality of hard tips to said distal end of said insertion member;
said insertion member with said selected one of said hard tips mounted thereon being insertable into said vein through said upstream incision and movable through said vein until said hard tip extends out of said downstream incision;
said selected one of said hard tips being replaceable with a second hard tip having a cutting blade which is chosen to facilitate removal of said valve from said vein, while said selected hard tip extends out of said second incision;
whereby upon withdrawal of said insertion member with said second hard tip attached thereto back through said vein, the chosen cutting blade will precisely incise said valve as said second hard tip passes said valve.

18. A venous valve-incising device according to claim 17, wherein:
said curved portion of each of said hard tips forms an acute angle with reference to said axis of said respective rod portion.

19. A venous valve-incising device according to claim 17, wherein said coupling means includes a male screw portion formed on one of said hard distal end of said insertion member and the rod portion of each of said plurality of tips, and a female screw portion formed on the other of said hard distal end of said insertion member and the rod portion of each of said plurality of hard tips.

20. A venous valve-incising device according to claim 19, wherein said male screw portion includes two screw parts.

21. A venous valve-incising device according to claim 17, wherein said coupling means comprises:
an insertion hole and slits formed in one of the hard distal end of the insertion member and the rod portion of each of said plurality of hard tips;
an insertion rod and engagement pins formed on the other of said hard distal end of the insertion member and the rod portion of each of said plurality of hard tips; and
said insertion rod being insertable into said insertion hole and said engagement pins fitting into respective slits upon insertion of said insertion rod into said insertion hole.

22. A venous valve-incising device according to claim 21, wherein said insertion hole and slits are formed in the rod portion of each of said plurality of hard tips.

* * * * *